United States Patent
Kahl

(10) Patent No.: US 6,221,004 B1
(45) Date of Patent: Apr. 24, 2001

(54) DEVICE FOR REDUCTION OF FLATULENCE

(76) Inventor: Melvin R. Kahl, 19 Carlotia Dr., Jeffersonville, IN (US) 47130

( * ) Notice: Subject to any disclaimer, the term of this patent is extended or adjusted under 35 U.S.C. 154(b) by 0 days.

(21) Appl. No.: 09/350,477

(22) Filed: Jul. 9, 1999

Related U.S. Application Data

(60) Provisional application No. 60/093,593, filed on Jul. 21, 1998.

(51) Int. Cl.[7] ....................................... A61F 2/00
(52) U.S. Cl. ................................................ 600/29
(58) Field of Search ............................ 600/29, 31, 32

(56) References Cited

U.S. PATENT DOCUMENTS

| 4,182,335 | 1/1980 | Matrullo . |
|---|---|---|
| 4,261,340 | 4/1981 | Baumel et al. . |
| 4,406,657 | 9/1983 | Curutcharry . |
| 4,943,276 | 7/1990 | Ghedina . |
| 5,800,338 | * 9/1998 | Kollerup et al. ........................ 600/29 |

\* cited by examiner

Primary Examiner—Eric F. Winakur
Assistant Examiner—Brian Szmal
(74) Attorney, Agent, or Firm—Theresa Fritz Camoriano; Camoriano and Associates

(57) ABSTRACT

A device to reduce flatulence includes a shaft with at least one axial groove in its outer surface. The shaft is enlarged and rounded at the insertion end. This enlarged end is inserted beyond the sphincter muscle. The muscle then closes in on shaft itself, but the grooves provides a path for the continual relief of gas pressure.

6 Claims, 4 Drawing Sheets

DEVICE FOR REDUCTION OF FLATULENCE

This application claims priority from Provisional Application Ser. No. 60/093,593, filed Jul. 21, 1998.

BACKGROUND OF THE INVENTION

The present invention relates to a device to reduce problems with discharge of intestinal gas. All individuals emit a certain amount of flatus or intestinal gas continually during the chemical action of the digestive process. The amount of intestinal gas depends to a large extent upon the diet and the particular digestive chemistry. Some individuals have a sphincter that does not seal completely, so they unconsciously pass or ooze small amounts of intestinal gas continually with no backup or pressure build up.

Some other individuals have a sphincter that seals against such leakage. For those people, as intestinal gas is formed, pressure builds up in the anal area. The pressure buildup may cause severe pain. When pressure builds up sufficiently, it exceeds the sealing properties of the sphincter at the anus, causing a sudden escape of a sizable volume of this intestinal gas under pressure. This sudden discharge of intestinal gases vibrates membranes near the anus causing noise which can be very embarrassing to the person. Some people also experience "brown spots" on the underwear in conjunction with such intestinal gas emissions.

The prior art (See Ghedina Patent 4,943,276) teaches a device with a hollow inner tube as a pathway for the relief of intestinal gases and has small openings to allow the intestinal gases to reach the thin, hollow inner tube. However, these small openings are easily plugged by excreta and other material in the digestive tract, rendering this device ineffective.

In summary, there is a need to reduce the discomfort, pain, and embarrassment associated with flatus emission, and to eliminate "brown spots" on the underwear. This invention solves these problems as is set forth below.

SUMMARY OF THE INVENTION

The present invention provides a device which breaks the gas sealing properties of the anus of the user, thus allowing a continual and controlled leaking or oozing of intestinal gases, thus preventing any pressure build-up.

The present invention utilizes a shaft with external grooves running the length of the shaft in order to help ensure that the pathway for the intestinal gases remains open. Adjacent to the first end of the shaft is an enlargement which serves as a trap to stop flow of excreta and which secures the device in its proper position while at the same time allowing the passage of intestinal gases. Along the exterior surface of the shaft and running along its length is at least one groove which runs from the first end towards the second end of said shaft, providing a path for intestinal gases to take so that they can escape continuously under control through the sphincter muscle and out the anus.

The second end of the shaft remains outside the body and may include any of a number of features that can be used to remove the device. It may also include a fibrous material which serves to filter the exiting intestinal gases and to stop any carryover which could lead to "brown spotting" of the underwear.

The invention will now be described in greater detail with reference to the accompanying figures.

DETAILED DESCRIPTION OF THE INVENTION

Figure 1:
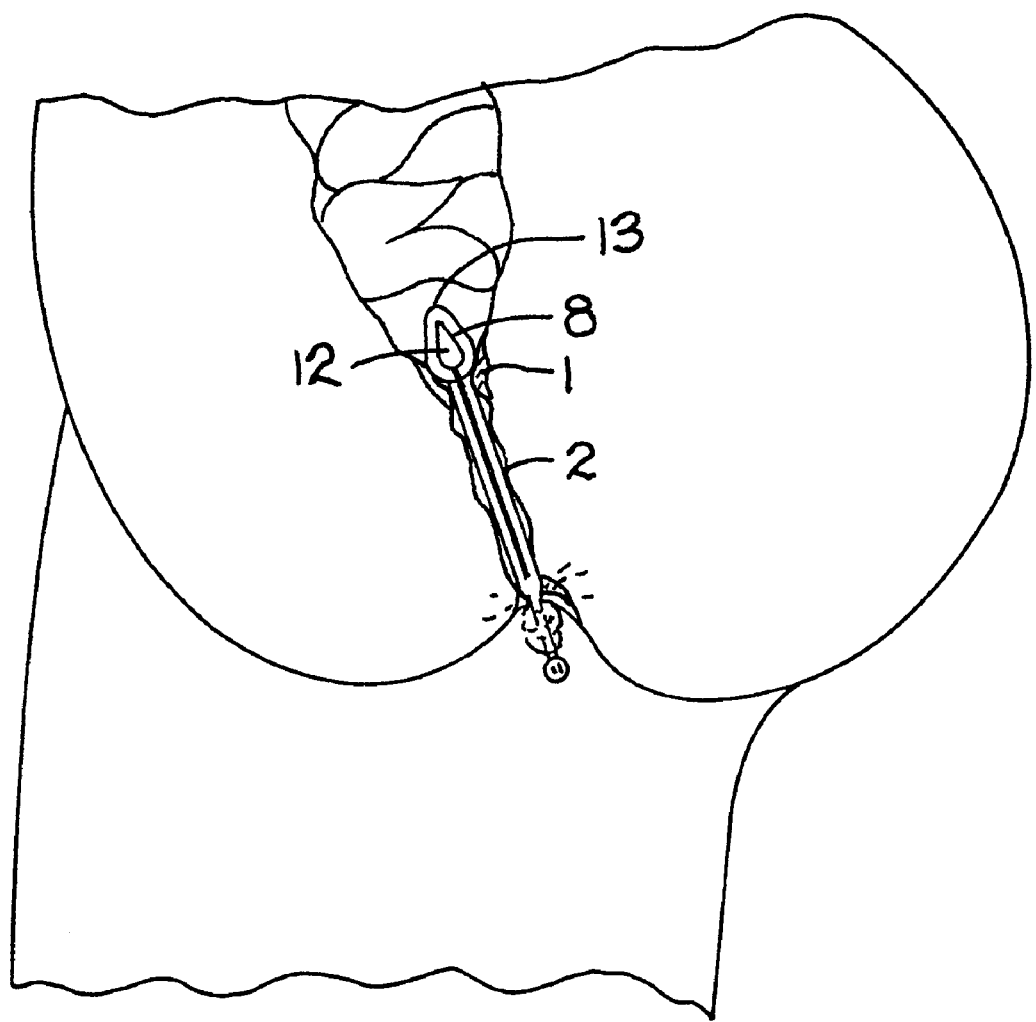
FIG. 1 is a schematic sectional view of one embodiment of the device installed in the anal canal.
Figure 1A:
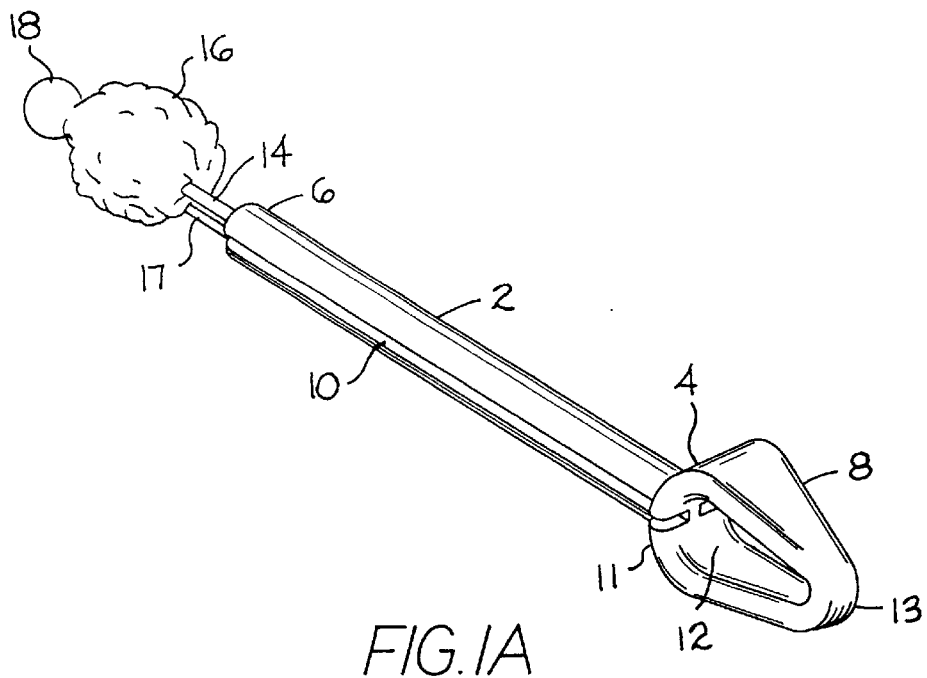
FIG. 1A is a perspective view of the device of FIG. 1.

As shown in FIGS. 1–7, the first embodiment of the present invention includes a shaft 2 with a first end 4 and a second end 6. Adjacent to the first end 4 is an enlargement 8 with a hollow section or recess 12. The enlargement 8 is generally oblong in shape with a rounded point at its first end 13 and a more blunt second end 11 which connects to the shaft 2. This generally oblong shape with a generally pointed first end 13 of the enlargement 8 allows for ease of insertion of this device through the sphincter muscle 1 of the user.

The shaft 2 has an outer surface, defining at least one groove 10, extending axially along its length from the first end 4 toward the second end 6 of the shaft 2. In this embodiment there are two opposed grooves 10. The grooves 10 extend axially beyond the first end 4 of the shaft 2, and beyond the blunt end 11 to the recess 12. The grooves provide the paths for the intestinal gases to escape past the sphincter muscle 1 of the user, so that the intestinal gases can continually leak, thereby continually relieving the intestinal gases and the pressure build-up and thus preventing a sudden discharge of said intestinal gases.

The enlargement 8 may have any of a number of different shapes, though in the preferred embodiment it will have the oblong shape discussed earlier, with a rounded point at its first end 13 for ease of insertion of the device through the sphincter muscle 1 of the user. The second end 11 of the enlargement 8 is connected to the shaft 2 at the first end 4 of the shaft 2. This second end 11 of the enlargement 8 will preferably have a wider, more blunt shape in contrast to the narrower first end 13 of said enlargement 8. This more blunt shape prevents "accidental" expulsion of the device, does not have the tendency to be trying to pry open the sphincter muscle 1 during usage, and yet will still allow for removal of the device with relative ease. The purpose of the recess 12 in the enlargement 8 is to act as a trap to provide for collecting small amounts of intestinal fluids and fecal matter and to reduce the potential clogging of the grooves 10.

Figure 2:
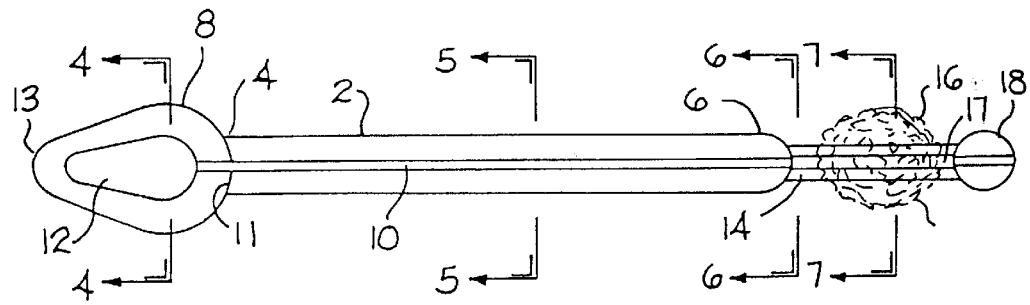
FIG. 2 is a top view of the device of FIG. 1.
Figure 3:
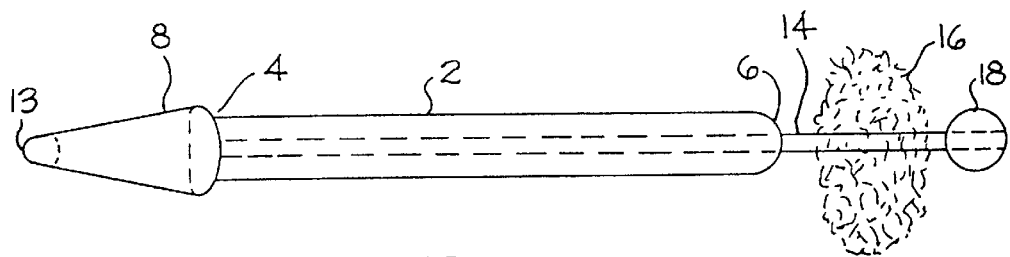
FIG. 3 is a side view of the embodiment of the device in FIG. 1.
Figure 4:
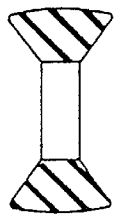
FIG. 4 is an enlarged sectional view taken along section 4—4 of FIG. 1.
Figure 5:
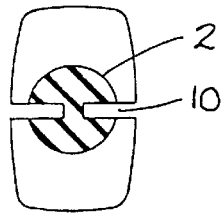
FIG. 5 is an enlarged sectional view taken along section 5—5 of FIG. 1.
Figure 6:
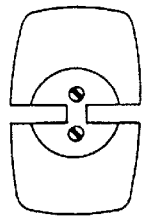
FIG. 6 is an enlarged sectional view taken along section 6—6 of FIG. 1.
Figure 7:
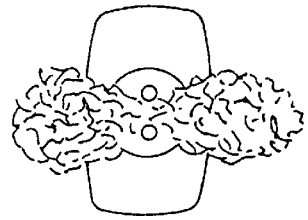
FIG. 7 is an enlarged sectional view taken along section 7—7 of FIG. 1.

Adjacent to the second end 6 of the shaft 2, there may be any of several mechanisms to aid in the removal of the device. FIGS. 2 and 3 show one embodiment in which there are two string-like extensions 14 attached at one end to the second end 6 of the shaft 2 and, at the other end, to a sphere 18. This design permits the string-like portions 14 to be molded together with the shaft 2, enlarged end 8, and sphere 18 as a single piece.

Adjacent to the second end 6 of the shaft 2, and extending through a slot 17 between the string-like extensions 14 is a mass of soft, fibrous material 16. This is an optional attachment. This fibrous material 16 may be a wad of sterilized cotton or other soft fibrous material, and it may be scented or otherwise treated to neutralize or offset the odors of the intestinal gases and/or of excreta which may have been carried over by the intestinal gases. The fibrous material 16 serves the main purpose of intercepting any excreta so as to minimize the possibility of "brown spotting" of the underwear.

When properly installed, the shaft is inserted in the rectum with the enlarged first end first, until the enlargement is just past the sphincter muscle. As soon as the enlargement 8 gets past the sphincter muscle 1 of the user, the sphincter muscle 1 closes in behind the enlargement 8 and around the shaft 2 at the first end 4 of the shaft 2. The grooves running axially along the shaft provide a path for intestinal gases to continually escape before the gases get a chance to build much pressure inside the intestines. The grooves along the shaft in essence provide a "leak" through the anus at the sphincter muscle, regardless of how leakproof the anus may be when the device is not installed.

The sphincter muscle 1 extends approximately 1½ inches from the anus. The length of the shaft 2 shall be such that it allows for the enlargement 8 to be inserted beyond the sphincter muscle 1, as well as for the shaft to provide the grooves necessary for the intestinal gases to escape. However, the length shall not be so long that it becomes an annoyance to the user. Typically, the shaft will be from one-and-one-half inches to three inches long.

Figure 1B:
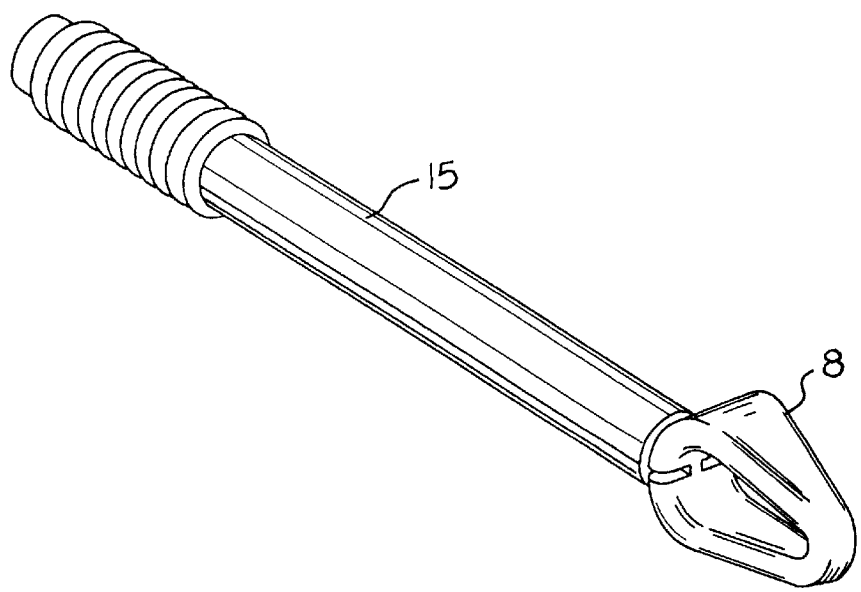
FIG. 1B is a perspective view of the device of FIG. 1A with an insertion sheath installed over the shaft.

In some instances, depending on the individual as well as on the type and rigidity of the materials of manufacture used for the device, the insertion of the device may be aided by the use of a tubular application sheath 15, shown in FIG. 1B. This sheath 15 provides support during the insertion of the device, provides a means for lubrication prior to application, and a means to prevent the lubricant from clogging the gas flow channels or grooves. Once the device has been inserted, the sheath 15 is removed.

Figure 8:
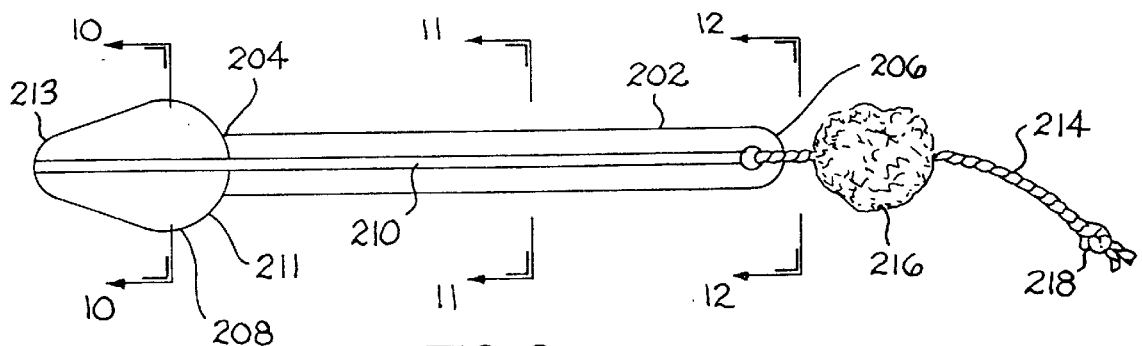
FIG. 8 is a top view of a second embodiment of the device of the present invention.
Figure 9:
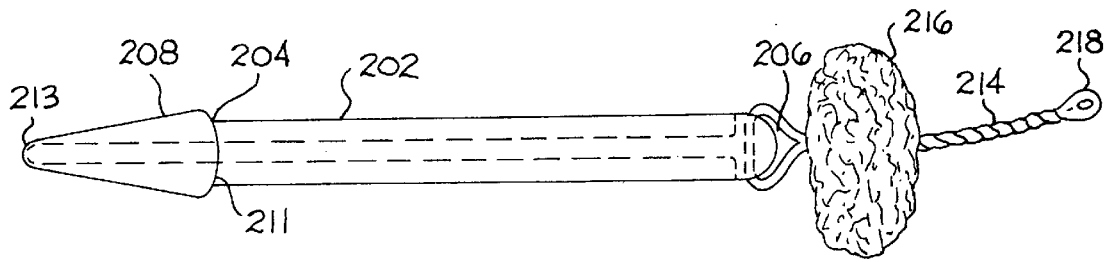
FIG. 9 is a side view of the embodiment of the device in FIG. 8.
Figure 10:
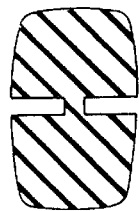
FIG. 10 is an enlarged sectional view taken along section 10—10 of FIG. 8.
Figure 11:
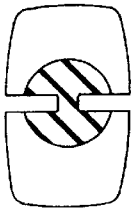
FIG. 11 is an enlarged sectional view taken along section 11—11 of FIG. 8.
Figure 12:
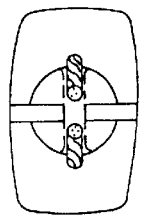
FIG. 12 is an enlarged sectional view taken along section 12—12 of FIG. 8.

FIGS. 8 and 9 show a second embodiment of the present invention. As in the first embodiment discussed above, this embodiment includes a thin, elongated shaft 202 with a first end 204 and a second end 206, an enlargement 208 with a rounded point at its first end 213 and a wider, more blunt second end 211, at least one groove 210, and absorbent material 216. The main differences between the first embodiment and this second embodiment are as follows:

First, the two string-like extensions 14 shown in FIGS. 2 and 3 have been replaced by a string 214 with a knot 218 tied at the end in lieu of a sphere 18. Second, the enlargement 208 is a solid piece which has no recessed area 12. Third, the groove 210 runs beyond the first end 204 of the shaft 202, to the pointed end 213 of the enlargement 208.

It will be obvious to those skilled in the art that modifications may be made to the embodiments described above without departing from the scope of the present invention.

What is claimed is:

1. A flatulence reduction device, comprising:
   a thin, elongated shaft having an outer surface and first and second ends;
   an enlarged portion adjacent to said first end; and
   at least one groove extending lengthwise along the outer surface of said shaft from said first end toward second end.

2. A flatulence reduction device as recited in claim 1, and further comprising a recess formed in said enlarged portion.

3. A flatulence reduction device as recited in claim 2, wherein said groove extends into said recess.

4. A flatulence reduction device as recited in claim 1, and further comprising a flexible string-like extension from the second end of said shaft.

5. A flatulence reduction device as recited in claim 1, and further comprising an absorbent material connected to said device adjacent the second end of said shaft.

6. A flatulence reduction device, comprising:
   a thin, elongated shaft extending between one-and-one-half and three inches and having an outer surface and first and second ends;
   an enlarged portion adjacent to said first end;
   at least one groove extending lengthwise along the outer surface of said shaft from said first end toward said second; and
   a flexible string-like extension from the second end of said shaft, wherein said shaft, enlarged portion, and string-like extension are molded as a single piece.

* * * * *